United States Patent
Salmon

(10) Patent No.: US 6,183,732 B1
(45) Date of Patent: Feb. 6, 2001

(54) CHEMICAL COMPOSITION

(75) Inventor: Michael Salmon, Frome (GB)

(73) Assignee: Johnson & Johnson Consumer Companies, Skillman, NJ (US)

( * ) Notice: Under 35 U.S.C. 154(b), the term of this patent shall be extended for 0 days.

(21) Appl. No.: 09/032,571

(22) Filed: Feb. 27, 1998

(30) Foreign Application Priority Data

Mar. 6, 1997 (GB) .................................... 9704643

(51) Int. Cl.$^7$ ........................... A61K 7/00; A61K 9/14
(52) U.S. Cl. ........................ 424/70.11; 424/401
(58) Field of Search ................... 424/401, 70.11

(56) References Cited

U.S. PATENT DOCUMENTS

| | | | |
|---|---|---|---|
| 4,994,088 | 2/1991 | Ando et al. | 8/426 |
| 5,009,880 | * 4/1991 | Grollier et al. | 424/47 |
| 5,124,078 | * 6/1992 | Baust | 252/546 |
| 5,476,660 | * 12/1995 | Somasundaran et al. | 424/401 |
| 5,650,384 | 7/1997 | Gordon et al. | 510/189 |

FOREIGN PATENT DOCUMENTS

| | | |
|---|---|---|
| 1266439 | 3/1990 | (CA) . |
| 2079098 | 10/1991 | (CA) . |
| 2093653 | 4/1992 | (CA) . |
| 2087140 | 7/1993 | (CA) . |
| 2131174 | 9/1993 | (CA) . |
| 2141328 | 2/1994 | (CA) . |
| 2141877 | 2/1994 | (CA) . |
| 2153313 | 8/1994 | (CA) . |
| 2155032 | 8/1994 | (CA) . |
| 2155766 | 8/1994 | (CA) . |
| 2174633 | 6/1995 | (CA) . |
| 2179520 | 6/1995 | (CA) . |
| 2180942 | 8/1995 | (CA) . |
| 2190739 | 2/1996 | (CA) . |
| 2190833 | 2/1996 | (CA) . |
| 2190607 | 5/1996 | (CA) . |
| 2143558 | 8/1996 | (CA) . |
| 78104478 | of 1981 | (TW) . |
| WO 94/17783 | 8/1994 | (WO) . |
| WO 98/31327 | 7/1998 | (WO) . |

* cited by examiner

*Primary Examiner*—Richard L. Raymond
*Assistant Examiner*—Hong Liu
(74) *Attorney, Agent, or Firm*—Michele G. Mangini

(57) ABSTRACT

A composition for use in a topical skin formulation such as a shower gel or a bath gel or a cream or lotion, comprises polyalcohol humectant, a mixture of at least two polyquaternary compounds, one of which is a cationic copolymer and one of which is an amphoteric copolymer, the copolymers being present in a weight ratio of cationic copolymer to amphoteric copolymer of 1:1.75 to 1:6, wherein the weight ratio of polyalcohol humectant to the said mixture lies in the range 1:0.06 to 1:0.1. When employed in a topical skin formulation the present combination of humectants provides an improved moisturizing effect.

10 Claims, No Drawings

CHEMICAL COMPOSITION

The present invention relates to a chemical composition, particularly although not exclusively, a chemical composition intended for personal washing.

The human skin comprises three physiologically different layers. The outermost layer is called the Epidermis and itself comprises an outer layer known as the Stratum Corneum made up of dead keratinised flattened cells and an inner layer known as the Basal layer which comprises cells that divide and migrate upwards to produce the Stratum Corneum.

The Epidermis thus comprises a dead avascular layer of stratified squamous epithelium. It gives important protection to the human body from assault by microbes, bacteria and fungi.

The Stratum Corneum forms the barrier between the internal body and the external environment and is responsible for maintaining normal water loss from the body to balance the water supply and the evaporation rate. The water content of the Stratum Corneum is an equilibrium between moisture gain and moisture loss. Moisture is gained in the skin as the cells divide and by the external addition to the skin of a cream, lotion or the like. Moisture is lost from the skin as it naturally dries out due to the external environment. Thus for the skin to gain moisture there must be a rise in the water content of the Stratum Corneum.

In order to reduce the amount of water lost to the external environment a traditional practice comprises applying a residual film of a composition including an occlusive agent or humectant to the skin's surface. An occlusive agent leaves a residual film which is a mechanical barrier preventing water from evaporating from the Stratum Corneum and from passing from the external environment through to the skin. A humectant however is a hygroscopic material which acts like a sponge, holding water close to the skin and permitting a higher level of water to be maintained in the Stratum Corneum.

Many humectants have been proposed in the past in a wide variety of skin care products. For example, WO 94/17783 (Unilever N.V.et al) describes a cleansing composition intended for use as a personal washing product, such as facial wash foams, bath foams and hair shampoos, in which the composition includes as a surfactant acyl glycolate and a cosurfactant, and optionally includes a humectant such as glycerine and a foam modifying agent such as cationic polymers for example polyquaternium-24 or polyquaternium-10.

It is an object of the present invention to provide a composition comprising a mixture of humectants having improved properties on application to human skin.

It is a further object of the present invention to provide a composition comprising a mixture of humectants and a surfactant for use in washing human skin.

It is a further object of the present invention to provide a composition in the form of a shower gel comprising a surfactant and a mixture of humectants, wherein the shower gel provides improved moisturising and skin feel effects.

According to the present invention, there is provided a composition for use in a topical skin formulation comprising:
(i) polyalcohol humectant;
(ii) a mixture of at least two polyquaternary compounds, one of which is a cationic copolymer and one of which is an amphoteric copolymer, the copolymers being present in a weight ratio of cationic copolymer to amphoteric copolymer of 1:1.75 to 1:6;

wherein the weight ratio of polyalcohol humectant to said mixture lies in the range 1:0.06 to 1:0.1.

The polyalcohol humectant is preferably selected from the group comprising glycerol, propylene glycol, butylene glycol and mixtures thereof. The polyalcohol humectant is suitably glycerol which has good moisturising properties with respect to the human skin.

When employed, however, as part for example of a shower gel the polyalcohol humectant which is water soluble can rapidly get removed when rinsing the skin. In order to increase the substantivity of for example the glycerol the cationic copolymer, which also acts as a moisturising agent, is suitably Polyquatemium-7 which is a copolymer of dimethyl diallyl ammonium chloride and acryl amide.

The amphoteric copolymer is suitably Polyquatemium-39 which is a 1:2:1 by weight terpolymer of acrylic acid, dimethyl diallyl ammonium chloride and acryl amide.

The amphoteric polymer contributes to the skin feel of the composition and its ease of application. The presence of the amphoteric polymer may potentially effect the ability of the cationic copolymer to increase the substantivity of the glycerol. By means of the present invention, however, the combination of at least the present three ingredients can provide a synergistic moisturising effect greater than the sum of the effect of each taken separately.

Preferably the weight ratio of cationic copolymer to amphoteric copolymer lies in the range 1:1.75 to 1:3. Ideally it is 1:2.

Suitably the composition contains a surfactant. The surfactant can be any surfactant or mixture of surfactants suitable for use in personal cleansing products. Suitably the surfactant is an anionic surfactant. Preferably the surfactant is sodium laureth sulphate.

Quaternised polymers are high molecular weight, water soluble polymers having cationic or amphoteric properties. Different polymers can have different levels of quaternisation. Quaternised polymers such as Polyquaternium 7 and Polyquatemium-39 are available commercially from a number of suppliers. They are available for example in the form of 10 wt % aqueous solutions from Chemviron Speciality Chemicals under their trade name "Merquat".

Particular examples suitable for use in the present invention include "Merquat S" which is 10 % aqueous solution of a highly charged cationic copolymer of dimethyl diallyl ammonium chloride and acryl amide having a molecular weight of $7 \times 10^6$ and a viscosity of 9000 to 15000 cps at 25° C. measured on a Brookfield RVF#4 spindle at 10 RPM, and "Merquat Plus 3330" which is 10 wt % aqueous solution of a polyampholyte terpolymer consisting of acrylic acid, dimethyl diallyl ammonium chloride and acryl amide in a 25:50:25 weight ratio of acrylic acid:DMDAAC:acryl amide, the terpolymer having a molecular weight of $4 \times 10^6$ and the solution having a viscosity of 4,400 to 10,400 cps at 25° C. measured using a Brookfield:LVF #4 spindle at 30 RPM.

Suitably the present composition comprises a composition comprising 10 to 20 wt % anionic surfactant, 1.5 to 6.0 wt % polyalcohol humectant, 0.225 to 0.425 wt % mixture of polyquaternary compounds and water. Preferably the cationic copolymer is present at a level between 0.025 wt % and 0.125 wt % and the amphoteric copolymer is present at a level between 0.175 wt % and 0.30 wt %.

Even more suitably the present composition comprises:
15 wt % sodium laureth sulphate
4 wt % glycerol
0.2 wt % of a 1:2:1 terpolymer of acrylic acid, dimethyl diallyl ammonium chloride and acryl amide 0.1 wt % of a copolymer of dimethyl diallyl ammonium chloride and acryl amide and water to 100%.

The weight per cent amounts of polyquaternary compounds recited are the absolute amounts present in the composition; not the quantity to be added in for example the form of aqueous solution supplied by the manufacturers.

Preferably the present composition is in the form of a shower gel or bath gel. Other forms are however not excluded and include bars, creams, lotions, sun care products, shaving creams, conditioners and the like. Minor ingredients can be included such as perfume, colour, pearlescer, thickener, pH modifier, sun block, preservative, etc.

The present compositions can be prepared by admixing the ingredients together.

Embodiments of the present invention will now be described by way of example only.

Sixteen compositions were prepared according to the formulation given in Table I.

TABLE I

|  | wt % |
|---|---|
| Empicol 0251\70J | 15 |
| Sodium chloride | qs |
| Euxyl K400 | 0.2 |
| Citric acid | qs |
| Glycerol | 4 |
| Merquat S | 0.5, 1.0, 1.5, 2.0 |
| Merquat Plus 3330 | 0.5, 1.0, 1.5, 2.0 |
| Purified water | to 100 |

Empicol 0251/70J is sodium laureth sulphate, Euxyl K400 is a mixture of methyl dibromo glucaronitrile and phenoxyethanol. Details of Merquat S and Merquat Plus 3330 are given above. The weight per cent content given in Table I of Merquat S and Merquat plus 3330 refers to the ingredients in the form of their 10 wt % aqueous solutions as supplied by the manufacturers.

In each case the formulations were prepared by firstly adding the Empicol to the water and stirring until fully dissolved, followed by adding the glycerol and stirring for ten minutes. Next the two Merquats were added followed by the Euxyl with further stirring. The resulting solution was buffered to pH 5.5 using citric acid and its viscosity increased with sodium chloride.

Altogether sixteen formulations were prepared at the four varying levels of Merquat S for each of the four levels Merquat Plus 3330.

Also prepared as controls were solutions A, B, C and D, given below:

Control A: formulation according to Table I omitting glycerol+Merquat S+Merquat Plus 3330.
Control B: 4 wt % solution glycerol.
Control C: 1 wt % solution Merquat S.
Control D: 2 wt % solution Merquat Plus 3330.

Each of the formulations in Table I as well as each of the controls was tested on forearm skin of a number of volunteers. A strict protocol was followed to ensure reliability of the results. The aim of each test was to measure the moisturisation effect of the product on human skin.

The test method involved the following steps:

1. The volunteer was acclimatised in the test room for at least ten minutes.
2. Uniform test squares were marked on the inner forearm.
3. A base line reading from each test square was taken using a Corneometer CM82 Skin Diagnosis Centre.
4. The inner forearm was wetted using lukewarm water.
5. 1 ml of product was applied to each test square using a small syringe (or cotton bud for the Controls).
6. The product was evenly distributed within each test square.
7. The product was left on the skin for 1.5 minutes.
8. The product was wiped off with a clean soft tissue.
9. An initial reading for each test square, using the Corneometer CM82 Skin Diagnosis Centre, was taken and a repeat reading was taken 10 minutes later.

The Corneometer CM82 Skin Diagnosis Centre (ex. Courage & Khazaka Electronic GmbH) is an instrument designed to measure skin moisture. The instrument includes a sensing probe which is placed on the test square skin surface and indicates the moisture degree on the skin surface by means of a capacity measurement. The measurements are automatically recorded.

From the results recorded a percent increase in moisturisation attributable to the test product was calculated. The amount of moisturisation increase was corrected to take account of transient changes in the skin and the amount of moisture that the skin gains from the detergent base formulation alone. The results are given in the Tables II and III below and are calculated as follows:

% Increase in Moisturisation=(Test-Base Line)−(Control A-Base line)

where

Test=Test reading after 10 minutes−Initial test reading/Initial reading×100

Base Line=No product after 10 minutes−Initial no product/Initial no product×100

Control A=Control A after 10 minutes−Initial Control A/Initial Control A×100

Table II gives the percent increase in moisturisation for the sixteen test products identified by their Merquat S and Merquat Plus 3330 wt % content.

TABLE II

|  | Merquat S | | | |
|---|---|---|---|---|
| Merquat Plus 3330 | 0.5 | 1.0 | 1.5 | 2.0 |
| 0.5 | 1.43 | 1.69 | −0.86 | 2.85 |
| 1.0 | −7.81 | 0.08 | −0.64 | 1.28 |
| 1.5 | −0.31 | 1.09 | 0.69 | 4.35 |
| 2.0 | 5.8 | 9.32 | 1.7 | 0.78 |

As can be seen from Table II, the greatest increase in moisturisation occurred at a level of 1 wt % Merquat S and 2.0 wt % Merquat Plus 3330.

Table III below gives the percent increase in moisturisation for Controls A, B, C. and D.

TABLE III

| Test Solution | % increase in moisturisation after 10 minutes |
|---|---|
| Control A | 2.65 |
| Control B | −2.14 |
| Control C | −2.17 |
| Control D | −1.39 |

A comparison of the figures in Table III with the results given in Table II for the formulation containing 4 wt % glycerol, 2 wt % Merquat Plus 3330 and 1 wt % Merquat S shows that the beneficial moisturisation effect on the skin of glycerol, Merquat S and Merquat Plus 3330 is only given when the ingredients are acting together in the formulation.

The level of glycerol was studied in a series of formulations according to that given in Table I, but with neither of the Merquats present, and with levels of glycerol of 1, 2, 3, 4 and 5 wt %. Each formulation prepared was tested on human skin according to the above protocol and the results obtained are given in Table IV below.

TABLE IV

| wt % glycerol | % moisturisation |
|---|---|
| 1 | 0.83 |
| 2 | 3.38 |
| 3 | 5.32 |
| 4 | 6.04 |
| 5 | 6.11 |

Thus in the present formulations the optimum level of glycerol was selected as 4 wt % having regard to efficacy and cost.

What is claimed is:

1. A composition for use in a topical skin formulation comprising:
   (i) polyalcohol humectant;
   (ii) a mixture of at least two polyquaternary compounds, one of which is a cationic copolymer and one of which is an amphoteric copolymer, the copolymers being present in a weight ratio of cationic copolymer to amphoteric copolymer of 1:1.75 to 1:6;
   wherein the weight ratio of polyalcohol humectant to said mixture lies in the range 1:0.06 to 1:0.1.

2. A composition according to claim 1 comprising a surfactant.

3. A composition according to claim 2 comprising 10 to 20 wt % anionic surfactant, 1.5 to 6.0 wt % polyalcohol humectant and 0.225 to 0.475 wt % mixture of polyquaternary compounds.

4. A composition according to claim 3 wherein the surfactant is sodium laureth sulphate.

5. A composition according to claim 3 wherein the polyalcohol humectant is selected from the group comprising glycerol, propylene glycol, butylene glycol and mixtures thereof.

6. A composition according to claim 1 wherein the cationic copolymer is a copolymer of dimethyl diallyl ammonium chloride and acryl amide.

7. A composition according to claim 1 wherein the amphoteric copolymer is a terpolymer of acrylic acid, dimethyl diallyl ammonium chloride and acryl amide.

8. A composition according to claim 1 comprising:
   15 wt % sodium laureth sulphate
   4 wt % glycerol
   0.2 wt % of a 1:2:1 terpolymer of acrylic acid, dimethyl diallyl ammonium chloride and acryl amide
   0.1 wt % of a copolymer of dimethyl diallyl ammonium chloride and acryl amide and water to 100%.

9. A composition according to claim 8 in the form of a shower gel or bath gel.

10. A composition according to claim 1 in the form of a cream or lotion.

* * * * *